United States Patent [19]

Cantatore et al.

[11] 4,316,025
[45] Feb. 16, 1982

[54] PIPERIDINE COMPOUNDS

[75] Inventors: Giuseppe Cantatore, Casalecchio di Reno; Paolo Cassandrini, Bologna, both of Italy

[73] Assignee: Chimosa Chimica Organica S.p.A., Bologna, Italy

[21] Appl. No.: 139,274

[22] Filed: Apr. 10, 1980

[30] Foreign Application Priority Data

Apr. 13, 1979 [IT] Italy ................................ 21841 A/79

[51] Int. Cl.$^3$ ......................................... C07D 401/14
[52] U.S. Cl. .................................... 544/364; 544/360; 544/121; 260/239.3 R; 260/244.4; 260/45.8 N
[58] Field of Search ...................... 260/244.4, 239.3 R; 544/360, 364, 12.1

[56] References Cited

U.S. PATENT DOCUMENTS

| | | | |
|---|---|---|---|
| 3,306,903 | 2/1967 | Jain et al. | 544/360 X |
| 3,734,883 | 5/1973 | Holt | 260/45.8 N |
| 3,919,234 | 11/1975 | Ramey et al. | 260/268 TR |
| 4,167,512 | 9/1979 | Lai et al. | 260/239.3 R |
| 4,190,571 | 2/1980 | Lai et al. | 544/360 X |
| 4,207,228 | 6/1980 | Lai et al. | 260/239.3 R |
| 4,238,388 | 12/1980 | Cantatore et al. | 260/239.3 R |

FOREIGN PATENT DOCUMENTS

| | | | |
|---|---|---|---|
| 208872 | 5/1960 | Austria | 260/239.3 R |
| 2398750 | 2/1979 | France . | |
| 1392249 | 4/1975 | United Kingdom . | |
| 1424430 | 2/1976 | United Kingdom | 260/239.3 R |
| 1529903 | 10/1978 | United Kingdom . | |

OTHER PUBLICATIONS

Klingsberg, Pyridine and Its Derivatives, Part Three, pp. 8-10 & 16-17, Interscience Publishers (1962).
Karrer, Organic Chemistry, Second English Edition, p. 901, Elsevier Publishing Co., Inc., NY (1946).

Primary Examiner—Robert T. Bond
Attorney, Agent, or Firm—Wenderoth, Lind & Ponack

[57] ABSTRACT

Compounds of the formula

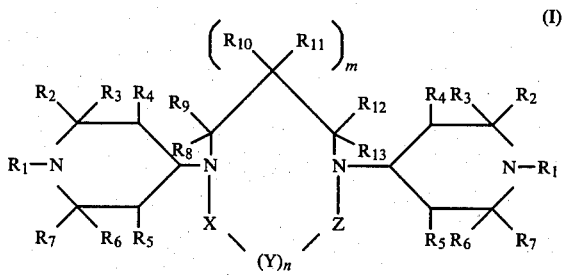

in which $R_1$ is hydrogen, —O•, —CN, a linear or branched alkyl radical containing from 1 to 20 carbon atoms, an alkenyl or alkynyl radical containing from 2 to 20 carbon atoms, benzyl which is unsubstituted or substituted by 1 to 3 $C_1$-$C_4$-alkyl radicals or hydroxybenzyl which is unsubstituted or substituted by 1 to 3 $C_1$-$C_4$-alkyl radicals; or $R_1$ is a —$COR_{14}$, —$COOR_{14}$, —$CH_2COOR_{14}$ or —$CONR_{14}R_{15}$ radical, in which $R_{14}$ and $R_{15}$, which may be identical or different, are linear or branched $C_1$-$C_{20}$-alkyl, $C_2$-$C_{20}$-alkenyl, $C_5$-$C_{12}$-cycloalkyl, phenyl which is unsubstituted or substituted by 1 to 3 $C_1$-$C_8$-alkyl radicals, hydroxyphenyl which is unsubstituted or substituted by 1 to 3 $C_1$-$C_4$-alkyl radicals, $C_7$-$C_{12}$-aralkyl, 2,2,6,6-tetramethyl-4-piperidyl, 1,2,2,6,6-pentamethyl-4-piperidyl or, when they are bonded to N, can be hydrogen or, conjointly with the N to which they are bonded, can form a nitrogen-containing heterocyclic ring with 5-7 members; or $R_1$ is a

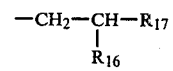

radical, in which $R_{16}$ is hydrogen or methyl and $R_{17}$ is —OH, —$OR_{14}$, —$OCOR_{14}$ or —$OCONR_{14}R_{15}$, in which $R_{14}$ and $R_{15}$ are as defined above; or $R_1$ is a

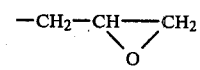

radical; $R_2$, $R_3$, $R_6$ and $R_7$, which may be identical or different, are an alkyl radical containing 1 to 6 carbon atoms; $R_4$ and $R_5$, which may be identical or different, are hydrogen or an alkyl radical containing from 1 to 6 carbon atoms; $R_8$, $R_9$, $R_{10}$, $R_{11}$, $R_{12}$ and $R_{13}$, which may be identical or different, are hydrogen or an alkyl radical containing 1 to 6 carbon atoms; m and n are zero or 1; X and Z, which may be identical or different, are

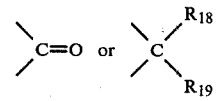

in which $R_{18}$ is hydrogen or $C_1$-$C_{20}$-alkyl and $R_{19}$ is hydrogen, $C_1$-$C_{20}$-alkyl or a —$(CH_2)_r$—$COOR_{14}$ radical, or a —$CONR_{14}R_{15}$ radical in which $R_{14}$ and $R_{15}$ are as defined above and r is an integer from 0 to 10; Y is

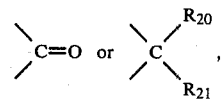

in which $R_{20}$ is hydrogen or $C_1$-$C_{20}$-alkyl and $R_{21}$ is hydrogen, $C_1$-$C_{20}$-alkyl, benzyl which is unsubstituted or substituted by 1 to 3 $C_1$-$C_4$-alkyl radicals, hydroxybenzyl which is unsubstituted or substituted by 1 to 3 $C_1$-$C_4$-alkyl radicals, 2,2,6,6-tetramethyl-4-piperidyl, 1,2,2,6,6-pentamethyl-4-piperidyl or a —OH, —$NO_2$, —$NR_{22}R_{23}$ or —NH—$COR_{24}$ radical, in which $R_{22}$ and $R_{23}$, which may be identical or different, are hydrogen, $C_1$-$C_{20}$-alkyl, benzyl or hydroxybenzyl substituted by 1 to 3 $C_1$-$C_4$-alkyl radicals and $R_{24}$ is $C_1$-$C_{20}$-alkyl, phenyl which is unsubstituted or substituted by 1 to 3 $C_1$-$C_8$-alkyl radicals or hydroxyphenyl which is substituted by 1 to 3 $C_1$-$C_4$-alkyl radicals, are useful as stabilizers for synthetic polymers.

6 Claims, No Drawings

PIPERIDINE COMPOUNDS

The present invention relates to novel piperidine compounds which can be used as light stabilisers, heat stabilisers and oxidation stabilisers for synthetic polymers, and to the process for their preparation.

More precisely, the present invention relates to novel compounds of the formula

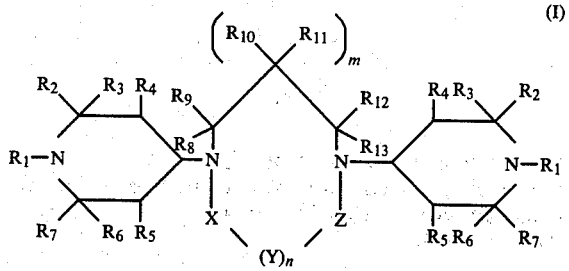

in which $R_1$ is hydrogen, $-O\bullet$, $-CN$, a linear or branched alkyl radical containing from 1 to 20 carbon atoms, an alkenyl or alkynyl radical containing from 2 to 20 carbon atoms, benzyl which is unsubstituted or substituted by 1 to 3 $C_1-C_4$-alkyl radicals or hydroxybenzyl which is unsubstituted or substituted by 1 to 3 $C_1-C_4$-alkyl radicals; or $R_1$ is a $-COR_{14}$, $-COOR_{14}$, $-CH_2COOR_{14}$ or $-CONR_{14}R_{15}$ radical, in which $R_{14}$ and $R_{15}$, which may be identical or different, are linear or branched $C_1-C_{20}$-alkyl, $C_2-C_{20}$-alkenyl, $C_5-C_{12}$-cycloalkyl, phenyl which is unsubstituted or substituted by 1 to 3 $C_1-C_8$-alkyl radicals, hydroxyphenyl which is unsubstituted or substituted by 1 to 3 $C_1-C_4$-alkyl radicals, $C_7-C_{12}$-aralkyl, 2,2,6,6-tetramethyl-4-piperidyl, 1,2,2,6,6-pentamethyl-4-piperidyl or, when they are bonded to N, can be hydrogen or, conjointly with the N to which they are bonded, can form a nitrogen-containing heterocyclic ring with 5–7 members; or $R_1$ is a

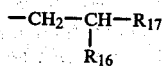

radical, in which $R_{16}$ is hydrogen or methyl and $R_{17}$ is $-OH$, $-OR_{14}$, $-OCOR_{14}$ or $-OCONR_{14}R_{15}$, in which $R_{14}$ and $R_{15}$ are as defined above; or $R_1$ is a

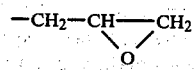

radical; $R_2$, $R_3$, $R_6$ and $R_7$, which may be identical or different, are an alkyl radical containing 1 to 6 carbon atoms; $R_4$ and $R_5$, which may be identical or different, are hydrogen or an alkyl radical containing from 1 to 6 carbon atoms; $R_8$, $R_9$, $R_{10}$, $R_{11}$, $R_{12}$ and $R_{13}$, which may be identical or different, are hydrogen or an alkyl radical containing 1 to 6 carbon atoms; m and n are zero or 1; X and Z, which may be identical or different, are

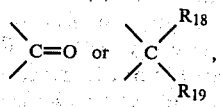

in which $R_{18}$ is hydrogen or $C_1-C_{20}$-alkyl and $R_{19}$ is hydrogen, $C_1-C_{20}$-alkyl or a $-(CH_2)_r-COOR_{14}$ radical, or a $-CONR_{14}R_{15}$ radical in which $R_{14}$ and $R_{15}$ are as defined above and r is an integer from 0 to 10; Y is

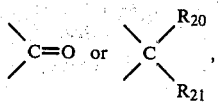

in which $R_{20}$ is hydrogen or $C_1-C_{20}$-alkyl and $R_{21}$ is hydrogen, $C_1-C_{20}$-alkyl, benzyl which is unsubstituted or substituted by 1 to 3 $C_1-C_4$-alkyl radicals, hydroxybenzyl which is unsubstituted or substituted by 1 to 3 $C_1-C_4$-alkyl radicals, 2,2,6,6-tetramethyl-4-piperidyl, 1,2,2,6,6-pentamethyl-4-piperidyl or a $-OH$, $-NO_2$, $-NR_{22}R_{23}$ or $-NH-COR_{24}$ radical, in which $R_{22}$ and $R_{23}$, which may be identical or different, are hydrogen, $C_1-C_{20}$-alkyl, benzyl or hydroxybenzyl substituted by 1 to 3 $C_1-C_4$-alkyl radicals and $R_{24}$ is $C_1-C_{20}$-alkyl, phenyl which is unsubstituted or substituted by 1 to 3 $C_1-C_8$-alkyl radicals or hydroxyphenyl which is substituted by 1 to 3 $C_1-C_4$-alkyl radicals.

The following are specific examples which illustrate the meanings of the various radicals:

$R_1$: hydrogen, $-O\bullet$, $-CN$, methyl, ethyl, n-propyl, n-butyl, isobutyl, n-hexyl, n-octyl, n-decyl, n-dodecyl, n-octadecyl, allyl, but-2-enyl, undec-10-enyl, oleyl, propargyl, benzyl, 4-methylbenzyl, 4-t-butylbenzyl, 4-hydroxybenzyl and 3,5-di-t-butyl-4-hydroxybenzyl;

$R_{14}$ and $R_{15}$: methyl, ethyl, n-propyl, n-butyl, n-hexyl, n-octyl, n-decyl, n-dodecyl, allyl, but-2-enyl, undec-10-enyl, oleyl, cyclohexyl, 2- and 4-methylcyclohexyl, 3,3,5-trimethyl-cyclohexyl, phenyl, 2- and 4-methylphenyl, 2,4- and 2,6-dimethylphenyl, 4-t-butylphenyl, 3,5-di-t-butyl-4-hydroxyphenyl, benzyl, 4-methylbenzyl, 4-t-butylbenzyl, 2,2,6,6-tetramethyl-4-piperidyl and 1,2,2,6,6-pentamethyl-4-piperidyl; furthermore, if $R_{14}$ and $R_{15}$ are bonded to a N, they are preferably hydrogen or, together with the N atom to which they are bonded, form part of, for example, a pyrrolidine, piperidine, morpholine, piperazine, N-methylpiperazine, homopiperazine or N-methylhomopiperazine ring.

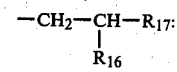

$-CH_2CH_2OH$; $-CH_2CHOHCH_3$, $-CH_2CH_2OCH_3$, $-CH_2CH_2OC_2H_5$, $-CH_2CH_2OC_4H_9$, $-CH_2CH_2OCOCH_3$, $-CH_2CH_2OCOC_3H_7$, $-CH_2CH_2OCON(CH_3)_2$ and $-CH_2CH_2OCON(C_2H_5)_2$.

$R_2$, $R_3$, $R_6$ and $R_7$: methyl and ethyl.

$R_4$, $R_5$, $R_8$, $R_9$, $R_{10}$, $R_{11}$, $R_{12}$ and $R_{13}$: hydrogen and methyl.

$R_{18}$, $R_{19}$, $R_{20}$, $R_{22}$ and $R_{23}$: hydrogen, methyl, ethyl, n-butyl, isobutyl, n-hexyl, n-octyl, n-decyl, n-dodecyl, n-hexadecyl and n-octadecyl.

$R_{21}$: hydrogen, methyl, ethyl, n-butyl, n-hexyl, n-octyl, n-decyl, n-dodecyl, n-hexadecyl, n-octadecyl, benzyl, 4-methylbenzyl, 4-t-butylbenzyl, 4-hydroxybenzyl, 3,5-di-t-butyl-4-hydroxybenzyl, $-OH$ and $-NO_2$.

$R_{24}$: methyl, ethyl, n-butyl, isobutyl, n-hexyl, n-octyl, n-decyl, n-dodecyl, n-hexadecyl, n-octadecyl, phenyl, 2- and 4-methylphenyl, 4-t-butylphenyl and 3,5-di-t-butyl-4-hydroxyphenyl.

Preferred compounds of the formula I are those in which $R_1$ is hydrogen or $C_1$–$C_6$-alkyl; $R_2$, $R_3$, $R_6$ and $R_7$ are methyl or ethyl; $R_4$, $R_5$, $R_8$, $R_9$, $R_{10}$, $R_{11}$, $R_{12}$ and $R_{13}$ are hydrogen or methyl; X and Z are

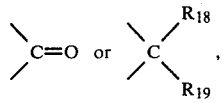

$R_{18}$ preferably being hydrogen or methyl and $R_{19}$ hydrogen or ethoxycarbonyl; Y is

in which $R_{20}$ is preferably hydrogen or $C_1$–$C_{12}$-alkyl and $R_{21}$ is hydrogen, $C_1$–$C_{12}$-alkyl, benzyl, 3,5-di-t-butyl-4-hydroxybenzyl, —OH, —$NO_2$ or —$NH_2$; and m and n are zero or 1.

More particularly preferred compounds of the formula I are those in which $R_2$ and $R_6$ are ethyl and $R_3$, $R_4$ and $R_7$ are methyl, and $R_5$ is hydrogen.

Especially preferred compounds of the formula I are those in which $R_2$, $R_3$, $R_6$ and $R_7$ are methyl and $R_4$ and $R_5$ are hydrogen.

The novel piperidine compounds of the present invention can be prepared by cyclisation of N,N'-bis(polyalkyl-4-piperidyl)-alkylenediamines of the formula

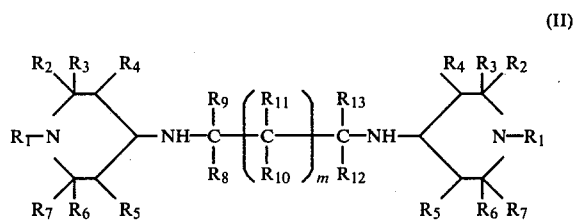

in which $R_1$, $R_2$, $R_3$, $R_4$, $R_5$, $R_6$, $R_7$, $R_8$, $R_9$, $R_{10}$, $R_{11}$, $R_{12}$ and $R_{13}$ are as defined above and m is 0 or 1.

The cyclisation is in general carried out by reaction with a compound of the type

in which X, Y, Z and n have the meanings already illustrated and A and B are halogen, preferably chlorine or bromine, or, only if X and Z are >C=O, can be a —$OR_{25}$ group, in which $R_{25}$ is $C_1$–$C_4$-alkyl, phenyl or methylphenyl.

Where X is

$R_{18}$ and $R_{19}$ being H or alkyl, and Z is >C=O, the compounds of the formula (I) can also be prepared by cyclisation of compounds of the formula (II) by reaction with compounds of the type

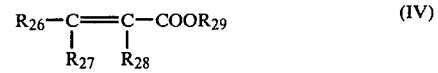

in which $R_{26}$, $R_{27}$ and $R_{28}$, which may be identical or different, are hydrogen or $C_1$–$C_4$-alkyl and $R_{29}$ is preferably $C_1$–$C_4$-alkyl, phenyl or methylphenyl.

Finally, in the particular case in which Y is

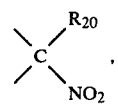

the compounds of the formula (I) can also be prepared by cyclisation of the compounds of the formula (II) with formaldehyde and nitro compounds of the formula (V)

in which $R_{20}$ is as defined above.

The nitro compounds thus obtained are preferably employed after reduction of the —$NO_2$ group to the —$NH_2$ group; this reduction can be carried out by various known methods, for example with hydrogen in the presence of a catalyst such as platinum, palladium or the like.

Preferred examples of compounds of the formula (III) which can be used for the preparation of the products of the formula (I) are: 1,2-dichloroethane, 1,2-dibromoethane, 1,2-dibromopropane, 1,2-dibromobutane, 1,2-dibromohexane, 1,2-dibromooctane, 1,3-dichloro-2-propanol, epichlorohydrin, ethyl 2,3-dibromopropionate, ethyl 2,3-dibromosuccinate, ethyl 3,4-dibromobutyrate, ethyl 10,11-dibromoundecanoate, ethyl 9,10-dibromostearate, methyl chloroacetate, ethyl bromoacetate, methyl 2-bromopropionate, methyl 2-bromobutyrate, methyl 2-bromocaproate, dimethyl oxalate, diethyl oxalate, dimethyl malonate, diethyl malonate, dimethyl ethylmalonate, dimethyl diethylmalonate, dimethyl n-butylmalonate, dimethyl isobutylmalonate, dimethyl n-hexylmalonate, dimethyl n-octylmalonate, dimethyl n-dodecylmalonate, dimethyl benzylmalonate and dimethyl 3,5-di-t-butyl-4-hydroxybenzylmalonate.

Examples of compounds of the formula (IV) are methyl acrylate, ethyl acrylate, methyl methacrylate, methyl 3,3-dimethylacrylate and methyl crotonate.

Examples of compounds of the formula (V) which can be used for the preparation of the compounds of the formula (I) are nitroethane, 1-nitropropane, 1-nitrobutane, 1-nitrohexane, 1-nitrooctane, 1-nitrodecane, 1-nitrododecane and 1-nitrooctadecane.

The compounds of the formula (I) in which $R_1$ has a meaning other than hydrogen can be obtained from dipiperidyl-diamines of the formula (II) which are already substituted on the piperidine NH groups, or by substitution of the NH groups of compounds of the formula (I) in which $R_1$ is hydrogen.

In this case, the compounds of the formula (I) in which $R_1$ is an oxyl radical can be obtained from the corresponding compounds in which $R_1$ is hydrogen by reaction with hydrogen peroxide in the presence of sodium tungstate, or by reaction with a per-acid, for example with m-chloroperbenzoic acid; the compounds in which $R_1$ is a —CN group can be obtained from the corresponding compounds in which $R_1$ is hydrogen by reaction with CNCl or CNBr; the compounds in which $R_1$ is an alkyl, alkenyl, alkynyl or benzyl group can be prepared from the corresponding compounds in which $R_1$ is hydrogen by reaction with an alkyl halide, alkenyl halide, alkynyl halide, benzyl halide or substituted benzyl halide; the compounds in which $R_1$ is methyl can also be prepared from the corresponding compounds in which $R_1$ is hydrogen by reaction with formaldehyde and formic acid (the Eschweiler-Clarke reaction; see Organic Reactions, Vol. V, page 307, Wiley & Sons, 1962); the compounds in which $R_1$ is a —$COR_{14}$, —$COOR_{14}$, —$CH_2COOR_{14}$ or —$CONR_{14}R_{15}$ group can be prepared from the corresponding compounds in which $R_1$ is hydrogen by reaction with a halogen compound of the type of E-$COR_{14}$, E-$COOR_{14}$, E-$CH_2COOR_{14}$ or E-$CONR_{14}R_{15}$, in which E is a halogen, preferably chlorine, bromine or iodine and $R_{14}$ and $R_{15}$ are as defined above; the compounds in which $R_1$ is $$-CH_2-CH-R_{17}$$
$$|$$
$$R_{16}$$

can be prepared from the corresponding compounds in which $R_1$ is hydrogen by reaction with ethylene oxide or propylene oxide if $R_{17}$ is OH; if $R_{17}$ is —$OR_{14}$, —O-$COR_{14}$ or —$OCONR_{14}R_{15}$, they can be prepared by a subsequent reaction of the hydroxyl compound with a halogen compound of the type of E-$R_{14}$, E-$COR_{14}$ or E-$CONR_{14}R_{15}$, in which E, $R_{14}$ and $R_{15}$ have the meaning defined above; the compounds in which $R_1$ is a 2,3-epoxypropyl group can be obtained by reaction of the corresponding compounds in which $R_1$ is hydrogen with epichlorohydrin and an alkali metal hydroxide.

The compounds of the formula (II), which are the starting materials for the process according to the present invention, are obtained by reductive substitution, in the presence of hydrogen and of a hydrogenation catalyst, of alkylenediamines of the formula (VI)

$$H_2N-\underset{R_8}{\overset{R_9}{\underset{|}{C}}}-\left[\underset{R_{10}}{\overset{R_{11}}{\underset{|}{C}}}\right]_n-\underset{R_{12}}{\overset{R_{13}}{\underset{|}{C}}}-NH_2 \quad (VI)$$

with a polyalkyl-4-piperidone of the formula

<p align="center">(VII)</p>

$$R_1-N\underset{R_7\quad R_6\quad R_5}{\overset{R_2\quad R_3\quad R_4}{\diagdown}}=O$$

as described in U.S. Pat. No. 3,480,635.

In order better to illustrate the present invention, there will now be described some examples of the preparation of the compounds of the formula (I), which examples are purely by way of illustration and do not imply any limitation.

EXAMPLE 1

338 g (1 mol) of N,N'-bis-(2,2,6,6-tetramethyl-4-piperidyl)-ethylenediamine, 206.6 g (1.1 mol) of 1,2-dibromoethane, 276.4 g (2 mols) of anhydrous potassium carbonate and 2,000 ml of toluene are heated under reflux for 30 hours.

The reaction mixture is filtered hot, concentrated and then cooled.

The crystalline precipitate obtained is filtered off and recrystallised from toluene.

A compound of the formula

[structure of compound]

is obtained in the form of white crystals melting at 198°–9° C.

Analysis for $C_{22}H_{44}N_4$: Calculated: C 72.47%; H 12.16%; N 15.36%. Found: C 71.78%; H 11.98%; N 15.28%.

EXAMPLE 2

72.9 g (0.2 mol) of N,N'-bis-(2,2,6,6-tetramethyl-4-piperidyl)-piperazine, prepared as described in Example 1, 35.7 g (0.66 mol) of 85% strength formic acid and 59.2 g (0.73 mol) of 37% strength formaldehyde are heated under reflux for 10 hours.

The reaction mixture is cooled and a solution of 20 g of sodium hydroxide in 200 ml of water is added; the precipitate obtained is filtered off, washed with water until the pH is neutral, dried and crystallised from toluene.

The compound of the formula

[structure of compound]

is obtained in the form of white crystals melting at 210°–212° C.

Analysis for $C_{24}H_{48}N_4$: Calculated: C 73.41%; H 12.32%; N 14.27%. Found: C 72.57%; H 12.16%; N 14.20%.

EXAMPLE 3

202.8 g (0.6 mol) of N,N'-bis-(2,2,6,6-tetramethyl-4-piperidyl)-ethylenediamine, 155.9 g (0.6 mol) of ethyl 2,3-dibromopropionate, 165.8 g (1.2 mols) of anhydrous potassium carbonate and 1,000 ml of dimethylformamide are heated under reflux for 16 hours. The reaction mixture is filtered hot and the filtrate is concentrated to dryness.

The crystalline residue obtained is recrystallised from n-hexane. The compound of the formula

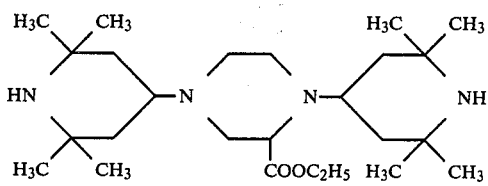

is obtained in the form of white crystals melting at 101°–2° C.

Analysis for $C_{25}H_{48}N_4O_2$: Calculated: C 68.76%; H 11.08%; N 12.83%. Found: C 68.12%; H 10.95%; N 12.65%.

EXAMPLE 4

70.4 g (0.2 mol) of N,N'-bis-(2,2,6,6-tetramethyl-4-piperidyl)-trimethylenediamine, 41.3 g (0.22 mol) of 1,2-dibromoethane, 55.3 g (0.4 mol) of anhydrous potassium carbonate and 500 ml of dimethylformamide are heated under reflux for 20 hours.

The mixture is filtered hot, the filtrate is evaporated to dryness and the crystalline residue obtained is recrystallised from n-hexane. The compound of the formula

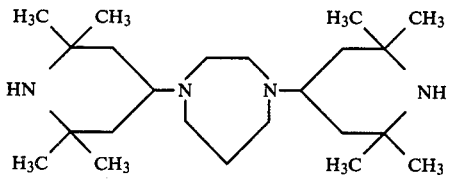

is obtained in the form of white crystals melting at 86°–7° C.

Analysis for $C_{23}H_{46}N_4$: Calculated: C 72.96%; H 12.24%; N 14.80%. Found: C 72.71%; H 12.15%; N 14.62%.

EXAMPLE 5

67.6 g (0.2 mol) of N,N'-bis-(2,2,6,6-tetramethyl-4-piperidyl)-ethylenediamine and 23.6 g (0.2 mol) of dimethyl oxalate are heated at 200° C. for 3 hours whilst removing the methanol liberated in the reaction.

The product obtained is crystallised from chloroform.

The compound of the formula

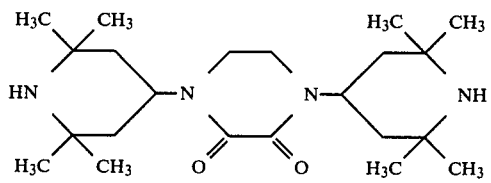

is obtained in the form of white crystals of melting point >300° C.

Analysis for $C_{22}H_{40}N_4O_2$: Calculated: C 67.31%; H 10.27%; N 14.27%. Found: C 66.47%; H 10.12%; N 14.16%.

EXAMPLE 6

135.2 g (0.4 mol) of N,N'-bis-(2,2,6,6-tetramethyl-4-piperidyl)-ethylenediamine, 49.7 g (0.4 mol) of chloroacetyl chloride and 800 ml of xylene are heated for 2 hours at 80° C.

A solution of 33.6 g (0.84 mol) of sodium hydroxide in 100 ml of water is then added and the mixture is heated under reflux for 8 hours. The aqueous phase is removed, the xylene layer is evaporated to dryness and the residue obtained is crystallised from n-octane. The compound of the formula

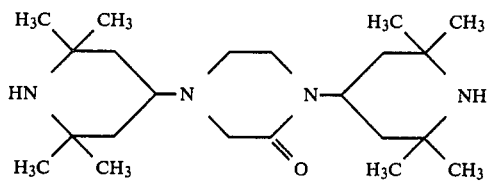

is obtained in the form of white crystals melting at 177°–8° C.

Analysis for $C_{22}H_{42}N_4O$: Calculated: C 69.79%; H 11.18%; N 14.80%. Found: C 68.95%; H 10.91%; N 14.64%.

EXAMPLE 7

135.2 g (0.4 mol) of N,N'-bis-(2,2,6,6-tetramethyl-4-piperidyl)-ethylenediamine, 37.84 g (0.44 mol) of methyl acrylate and 100 ml of methanol are heated under reflux for 6 hours, the solvent is then removed and the mixture is heated at 200° C. for 16 hours.

The product obtained is crystallised from isopropanol.

The compound of the formula

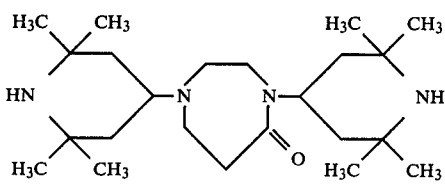

is obtained in the form of white crystals melting at 203°–5° C.

Analysis for $C_{23}H_{44}N_4O$: Calculated: C 70.36%; H 11.29%; N 14.27%. Found: C 69.75%; H 11.17%; N 14.13%.

EXAMPLE 8

33.8 g (0.1 mol) of N,N'-bis-(2,2,6,6-tetramethyl-4-piperidyl)-ethylenediamine and 14.5 g (0.11 mol) of dimethyl malonate are heated at 170°–180° C. for 3 hours whilst removing the methanol liberated by the reaction.

The product obtained is crystallised from isopropanol.

The compound of the formula

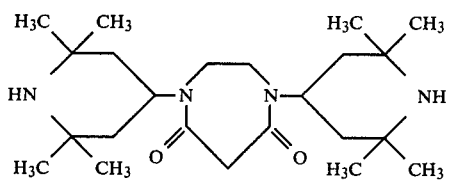

is obtained in the form of white crystals of melting point >300° C.

Analysis for $C_{23}H_{42}N_4O_2$: Calculated: C 67.94%; H 10.41%; N 13.78%. Found: C 67.38%; H 10.29%; N 13.73%.

EXAMPLE 9

35.2 g (0.1 mol) of N,N'-bis-(2,2,6,6-tetramethyl-4-piperidyl)-1,2-diaminopropane and 14.5 g (0.11 mol) of dimethyl malonate are heated at 170°-180° C. for 3 hours whilst removing the methanol liberated in the reaction.

The product obtained is crystallized from isopropanol.

The compound of the formula

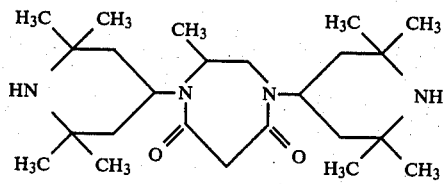

is obtained in the form of white crystals of melting point >300° C.

Analysis for C$_{24}$H$_{44}$N$_4$O$_2$. Calculated: C 68.53%; H 10.54%; N 13.32%. Found: C 67.75% H 10.39%; N 13.29%.

EXAMPLE 10

135.2 g (0.4 mol) of N,N'-bis-(2,2,6,6-tetramethyl-4-piperidyl)-ethylenediamine and 95 g (0.44 mol) of diethyl n-butylmalonate are heated at 200°-210° C. for 30 hours whilst removing the ethanol liberated in the reaction. The product obtained is crystallised from isopropanol.

The compound of the formula

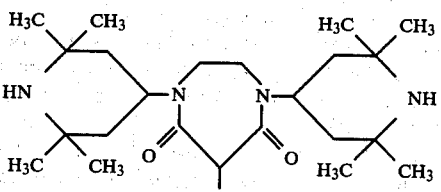

is obtained in the form of white crystals melting at 215°-7° C.

Analysis for C$_{27}$H$_{50}$N$_4$O$_2$: Calculated: C 70.08%; H 10.89%; N 12.11%. Found: C 69.06%; H 11.06%; N 11.94%.

EXAMPLE 11

67.6 g (0.2 mol) of N,N'-bis-(2,2,6,6-tetramethyl-4-piperidyl)-ethylenediamine, 12 g (0.4 mol) of paraformaldehyde, 15 g (0.2 mol) of nitroethane and 200 ml of methanol are heated at 50°-60° C. for 12 hours. The resulting mixture is evaporated to dryness and the residue is crystallised from n-hexane.

The compound of the formula

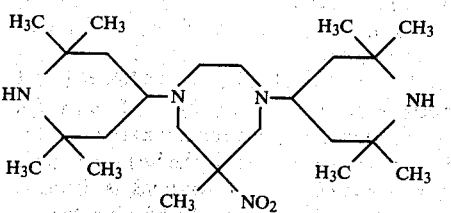

is obtained in the form of white crystals melting at 147°-9° C.

Analysis for C$_{24}$H$_{47}$N$_5$O$_2$: Calculated: C 65.86%; H 10.82%; N 16.00%. Found: C 65.40%; H 11.17%; N 15.74%.

EXAMPLE 12

81.2 g (0.2 mol) of 1,4-bis-(2,2,6,6-tetramethyl-4-piperidyl)-5,7-homopiperazinedione, prepared as described in Example 8, 36 g (1.2 mols) of paraformaldehyde and 500 ml of methanol are left to stand at ambient temperature for 2 days, with occasional stirring; the mixture is then hydrogenated at 50°-60° C. under a pressure of 10 atmospheres in the presence of 5 g of 10% strength palladium on charcoal.

The catalyst is separated off, the solvent is removed by distillation and the residue is crystallised from isopropanol.

The compound of the formula

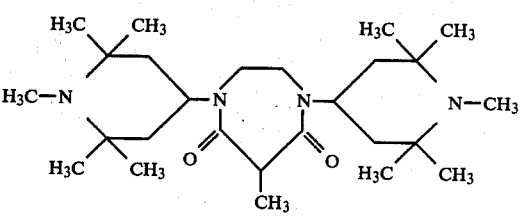

is obtained in the form of white crystals melting at 232°-3° C.

Analysis for C$_{26}$H$_{48}$N$_4$O$_2$: Calculated: C 69.60%; H 10.78%; H 12.49%. Found: C 69.86%; H 10.72%; N 12.21%.

EXAMPLE 13

67.6 g (0.2 mol) of N,N'-bis-(2,2,6,6-tetramethyl-4-piperidyl)-ethylenediamine and 37.6 g (0.2 mol) of dimethyl isobutylmalonate are heated at 160°-170° C. for 16 hours and at 220° C. for 2 hours, with removal of the methanol liberated by the reaction.

The reaction mixture is poured into water and the precipitate obtained is filtered off, washed with water, dried and then crystallised from acetone.

The compound of the formula

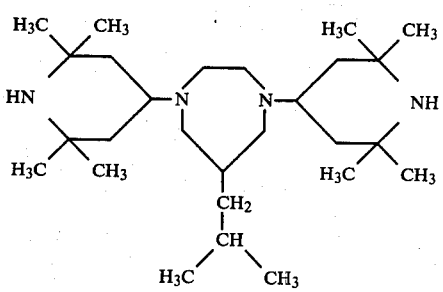

is obtained in the form of white crystals melting at 221°-2° C.

Analysis for C$_{27}$H$_{50}$N$_4$O$_2$: Calculated: C 70.08%; H 10.89%; N 12.11%. Found: C 69.56%; H 10.77%; N 11.74%.

EXAMPLE 14

2.3 g (0.1 gram atom) of sodium are added to a mixture of 40.6 g (0.1 mol) of 1,4-bis-(2,2,6,6-tetramethyl-4-piperidyl)-5,7-homopiperazinedione, prepared as described in Example 8, 100 ml of xylene and 100 ml of methanol. The mixture is stirred at ambient temperature until the sodium has reacted completely, and the methanol is then distilled off by heating to 140° C. The residue is cooled to 80° C., 29 g (0.15 mol) of n-octyl bromide are added and the batch is then heated under reflux for 22 hours. The reaction mixture is filtered hot and the filtrate is cooled to ambient temperature; the crystalline precipitate obtained is filtered off and is twice recrystallised from n-octane.

The compound of the formula

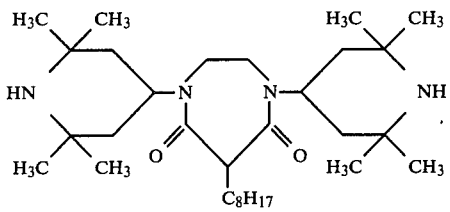

is obtained in the form of white crystals melting at 141°-2° C.

Analysis for $C_{31}H_{58}N_4O_2$: Calculated: C 71.76%; H 11.27%; N 10.80%. Found: C 70.63%; H 11.23%; N 10.35%.

EXAMPLE 15

40.6 g (0.1 mol) of 1,4-bis-(2,2,6,6-tetramethyl-4-piperidyl)-5,7-homopiperazinedione, prepared as described in Example 8, 36.7 g (0.1 mol) of 3,5-di-t-butyl-4-hydroxybenzyl diethyldithiocarbamate and 500 ml of isopropanol are heated at 70° C., a solution of 4 g of NaOH in 40 ml of water is added in 15 minutes and the mixture is heated under reflux for 4 hours. It is then cooled to 50° C., a solution of 12 g of acetic acid in 120 ml of water is added, the reaction mixture is then evaporated to dryness and the residue is crystallised twice from toluene.

The compound of the formula

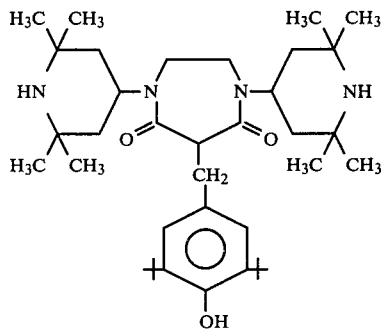

is obtained in the form of white crystals melting at 247°-9° C.

Analysis for $C_{38}H_{64}N_4O_3$: Calculated: C 73.03%; H 10.32%; N 9.87%. Found: C 73.09%; H 10.20%; N 9.71%.

EXAMPLE 16

36.4 g (0.1 mol) of N,N'-bis-(2,2,6,6-tetramethyl-4-piperidyl)-piperazine (prepared as described in Example 1), 30.6 g (0.3 mol) of acetic anhydride, 60.6 g (0.6 mol) of triethylamine and 100 ml of toluene are heated under reflux for 15 hours.

After cooling, 100 ml of water are added, the mixture is stirred for 15 minutes and the crystalline residue is then filtered off, washed with water, dried and crystallised from isopropanol.

The compound of the formula

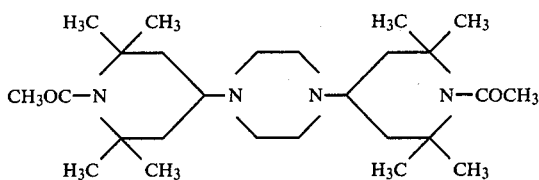

is obtained in the form of white crystals melting at 181°-2° C.

Analysis for $C_{26}H_{48}N_4O_2$: Calculated: C 69.60%; H 10.78%; N 12.49%. Found: C 69.36%; H 10.86%; N 12.37%.

As mentioned at the outset the compounds of the formula (I) are very efficient in improving the light resistance, heat resistance and oxidation resistance of synthetic polymers such as, for example, high density and low density polyethylene, polypropylene, ethylene-propylene copolymers, ethylene/vinyl acetate copolymers, polybutadiene, polyisoprene, polystyrene, butadiene/styrene copolymers, acrylonitrile/-butadiene/styrene copolymers, vinyl chloride and vinylidene chloride polymers and copolymers, polyoxymethylene, polyurethanes, saturated and unsaturated polyesters, polyamides, polycarbonates, polyacrylates, alkyd resins and epoxide resins.

The compounds of the formula (I) can be employed in the mixture with the synthetic polymers in various proportions depending on the nature of the polymer, the final use and the presence of other additives. In general, an appropriate amount to employ is from 0.01 to 5% by weight of the compounds of the formula (I) relative to the weight of the polymers, preferably from 0.1 to 1%.

The compounds of the formula (I) can be incorporated into the polymeric materials by various processes, such as dry mixing in the form of powders, or wet mixing in the form of a solution or suspension, or mixing in the form of a masterbatch; in these operations, the synthetic polymer can be employed in the form of powders, granules, solutions, suspensions or emulsions. The polymers stabilised with the products of the formula (I) can be used for the preparation of mouldings, film, tapes, fibres, monofilaments, lacquers and the like. Other additives may, if desired, be introduced into the mixtures of the compounds of the formula (I) with the synthetic polymers, examples of such other additives being antioxidants, UV absorbers, nickel-based stabilisers, pigments, fillers, plasticisers, antistatic agents, flameproofing agents, lubricants, anti-corrosion agents and metal deactivators. Examples of additives which can be employed in mixtures with the compounds of the formula (I) are, in particular:

Phenolic antioxidants, such as, for example, 2,6-di-t-butyl-p-cresol, 4,4'-thio-bis-(3-methyl-6-t-butylphenol), 1,1,3-tris-(2-methyl-4-hydroxy-5-t-butylphenyl)butane, octadecyl 3-(3,5-di-t-butyl-4-hydroxyphenyl)propionate, pentaerythritol tetra-(3,5-di-t-butyl-4-hydroxyphenyl)-propionate, tris-(3,5-di-t-butyl-4-hydroxybenzyl) isocyanurate and tris-(4-t-butyl-3-hydroxy-2,6-dimethylbenzyl) isocyanurate;

Secondary antioxidants such as esters of thiodipropionic acid, for example di-n-dodecyl thiodipropionate and di-n-octadecyl thiodipropionate; aliphatic sulfides and disulfides, for example di-n-dodecyl sulfide, di-n-octadecyl sulfide and di-n-octadecyl disulfide; aliphatic, aromatic and aliphatic-aromatic phosphites and thiophosphites, for example tri-n-dodecyl phosphite, tris-(nonylphenyl) phosphite, tri-n-dodecyl trithiophosphite, phenyl di-n-decyl-phosphite, di-n-octadecyl pentaerythritol diphosphite, tris-(2,4-di-t-butylphenyl) phosphite and tetrakis-(2,4-di-t-butylphenyl) 4,4'-biphenylenediphosphonite;

UV absorbers, for example 2-hydroxy-4-n-octoxybenzophenone, 2-hydroxy-4-n-dodecoxybenzophenone, 2-(2-hydroxy-3,5-di-t-butylphenyl)-5-chlorobenzotriazole, 2-(2-hydroxy-3,5-di-t-amylphenyl)-benzotriazole, 2,4-di-t-butylphenyl 3,5-di-t-butyl-4-hydroxybenzoate, phenyl salicylate, p-t-butylphenyl salicylate, 2,2'-di-n-octoxy-5,5'-di-t-butyloxanilide and 2-ethoxy-5-t-butyl-2'-ethoxyoxanilide;

Nickel-based light stabilisers, for example Ni monoethyl 3,5-di-t-butyl-4-hydroxybenzyl phosphonate, the butylamine-Ni 2,2'-thio-bis-(4-t-octylphenolate) complex, Ni 2,2'-thio-bis-(4-t-octylphenylphenolate), Ni dibutyldithiocarbamate, Ni 3,5-di-t-butyl-4-hydroxybenzoate and the Ni complex of 2-hydroxy-4-n-octoxybenzophenone;

Organo-tin stabilisers, for example dibutyl-tin maleate, dibutyl-tin laurate and dioctyl-tin maleate;

Acrylic esters, for example ethyl $\alpha$-cyano-$\beta,\beta$-diphenyl-acrylate and methyl $\alpha$-cyano-$\beta$-methyl-4-methoxycinnamate;

Metal salts of higher fatty acids, for example the stearates of calcium, barium, cadmium, zinc, lead and nickel and the laurates of calcium, cadmium, zinc and barium;

Organic and inorganic pigments, for example Color Index Pigment Yellow 37, Color Index Pigment Yellow 83, Color Index Pigment Red 144, Color Index Pigment Red 48:3, Color Index Pigment Blue 15, Color Index Pigment Green 7, titanium dioxide, iron oxide and the like.

The efficiency, as stabilisers, of the products prepared according to the present invention is illustrated in the examples which follow, in which the products obtained in the preparation examples are employed in a synthetic polymer composition.

The results are recorded in comparison with those obtained by adding known commercially available stabilisers.

EXAMPLE 17

2 g of each of the compounds indicated in Table 1 and 1 g of 2,6-di-t-butyl-p-cresol (antioxidant) are thoroughly mixed with 1,000 g of polypropylene of melt index 3.2 (Moplen C, a product of Società Montedison) and 1 g of calcium stearate.

The mixture obtained is then extruded at a temperature of 200°–230° C. and converted to granules, from which tapes having a thickness of 40 μm and a width of 3 mm are produced. The working conditions are as follows:

| | |
|---|---|
| extruder temperature: | 230–240° C. |
| head temperature: | 240° C. |

| | |
|---|---|
| -continued | |
| stretch ratio: | 1:6 |

The tapes obtained are exposed in a Weather-Ometer 65 WR (ASTM G27-70) with the temperature of the black panel at 63° C. Samples are taken periodically and the residual tensile strength of these is measured by means of a tensometer at constant speed; the exposure time required to halve the initial tensile strength ($T_{50}$) is then determined.

For comparison, a tape is prepared under the same conditions with the addition of 2 g of 2-hydroxy-4-n-octoxybenzophenone as a light stabiliser.

The results obtained are recorded in Table 1.

TABLE 1

| Stabiliser | $T_{50}$ (hours) |
|---|---|
| 2-Hydroxy-4-n-octoxybenzophenone | 300 |
| Compound of Example 1 | 2,180 |
| Compound of Example 2 | 2,090 |
| Compound of Example 3 | 1,850 |
| Compound of Example 4 | 1,970 |
| Compound of Example 6 | 1,330 |
| Compound of Example 10 | 1,450 |

EXAMPLE 18

2 g of each of the compounds indicated in Table 2 are thoroughly mixed with 1,000 g of high density polyethylene of melt index 0.32 (Moplen RO ZB-5000, a product of Società Montedison), 0.5 g of di-n-octadecyl 3-(3,5-di-t-butyl-4-hydroxyphenyl)-propionate (antioxidant) and 1 g of calcium stearate.

The mixture obtained is then extruded at a temperature of 190° C. and converted to granules from which discs of thickness 0.2 mm are produced by compression moulding at 200° C. The discs are exposed in a Weather-Ometer 65 WR with the black panel at a temperature of 63° C., and the increase in carbonyl groups ($\Delta CO$) is checked periodically, employing non-exposed samples to compensate for the initial absorption of the polymer. The time (T 0.1) required to obtain a $\Delta CO\%$ of 0.1 at 5.85 μm is calculated.

For comparison, polymer discs are prepared under the same conditions
 (a) without addition of a light stabiliser and
 (b) with the addition of 2 g of 2-hydroxy-4-n-octoxybenzophenone as a light stabiliser.

The results obtained are recorded in Table 2.

TABLE 2

| Stabiliser | T 0.1 (hours) |
|---|---|
| Without light stabiliser | 320 |
| 2-Hydroxy-4-n-octoxybenzophenone | 1,000 |
| Compound of Example 1 | >8,900 |
| Compound of Example 2 | >8,500 |
| Compound of Example 3 | >7,750 |
| Compound of Example 4 | >8,760 |
| Compound of Example 8 | >6,300 |
| Compound of Example 10 | >5,730 |

What is claimed is:
1. A compound of the formula

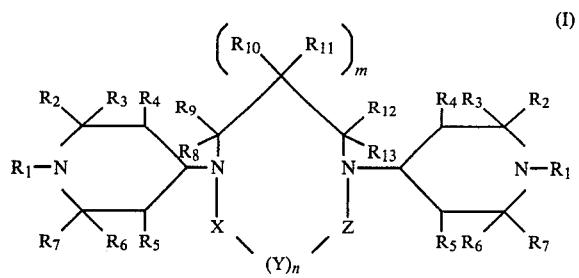

(I)

in which $R_1$ is hydrogen, $-O^\bullet$, $-CN$, a linear or branched alkyl radical containing from 1 to 20 carbon atoms, an alkenyl or alkynyl radical containing from 2 to 20 carbon atoms, benzyl which is unsubstituted or substituted by 1 to 3 $C_1-C_4$-alkyl radicals or hydroxybenzyl which is unsubstituted or substituted by 1 to 3 $C_1-C_4$-alkyl radicals; or $R_1$ is a $-COR_{14}$, $-COOR_{14}$, $-CH_2COOR_{14}$ or $-CONR_{14}R_{15}$ radical, in which $R_{14}$ and $R_{15}$, which may be identical or different, are linear or branched $C_1-C_{20}$-alkyl, $C_2-C_{20}$-alkenyl, $C_5-C_{12}$-cycloalkyl, phenyl which is unsubstituted or substituted by 1 to 3 $C_1-C_8$-alkyl radicals, hydroxyphenyl which is unsubstituted or substituted by 1 to 3 $C_1-C_4$-alkyl radicals, $C_7-C_{12}$-aralkyl, 2,2,6,6-tetramethyl-4-piperidyl, 1,2,2,6,6-pentamethyl-4-piperidyl or, when they are bonded to N, can be hydrogen or, conjointly with the N to which they are bonded, can form a nitrogen-containing heterocyclic ring selected from the group consisting of pyrrolidine, piperidine, morpholine, piperazine, N-methylpiperazine, homopiperazine and N-methylhomopiperazine; or $R_1$ is a

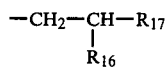

radical, in which $R_{16}$ is hydrogen or methyl and $R_{17}$ is $-OH$, $-OR_{14}$, $-OCOR_{14}$ or $-OCONR_{14}R_{15}$, in which $R_{14}$ and $R_{15}$ are as defined above; or $R_1$ is a

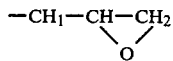

radical; $R_2$, $R_2$, $R_6$ and $R_7$, which may be identical or different, are an alkyl radical containing 1 to 6 carbon atoms; $R_4$ and $R_5$, which may be identical or different, are hydrogen or an alkyl radical containing from 1 to 6 carbon atoms; $R_8$, $R_9$, $R_{10}$, $R_{11}$, $R_{12}$ and $R_{13}$, which may be identical or different, are hydrogen or an alkyl radical containing 1 to 6 carbon atoms; m and n are zero or 1; X and Z, which may be identical or different, are

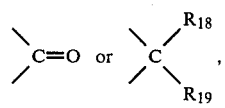

in which $R_{18}$ is hydrogen or $C_1-C_{20}$-alkyl and $R_{19}$ is hydrogen, $C_1-C_{20}$-alkyl or a $-(CH_2)_r-COOR_{14}$ radical, or a $-CONR_{14}R_{15}$ radical in which $R_{14}$ and $R_{15}$ are as defined above and r is an integer from 0 to 10; Y is

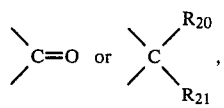

in which $R_{20}$ is hydrogen or $C_1-C_{20}$-alkyl and $R_{21}$ is hydrogen, $C_1-C_{20}$-alkyl, benzyl which is unsubstituted or substituted by 1 to 3 $C_1-C_4$-alkyl radicals, hydroxybenzyl which is unsubstituted or substituted by 1 to 3 $C_1-C_4$-alkyl radicals, 2,2,6,6-tetramethyl-4-piperidyl, 1,2,2,6,6-pentamethyl-4-piperidyl or a $-OH$, $-NO_2$, $-NR_{22}R_{23}$ or $-NH-COR_{24}$ radical, in which $R_{22}$ and $R_{23}$, which may be identical or different, are hydrogen, $C_1-C_{20}$-alkyl, benzyl or hydroxybenzyl substituted by 1 to 3 $C_1-C_4$-alkyl radicals and $R_{24}$ is $C_1-C_{20}$-alkyl, phenyl which is unsubstituted or substituted by 1 to 3 $C_1-C_8$-alkyl radicals or hydroxyphenyl which is substituted by 1 to 3 $C_1-C_4$-alkyl radicals.

2. A compound according to claim 1, of the formula I, in which $R_1$ is hydrogen or $C_1-C_6$-alkyl, $R_2$, $R_3$, $R_6$ and $R_7$ are methyl or ethyl, $R_4$, $R_5$, $R_8$, $R_9$, $R_{10}$, $R_{11}$, $R_{12}$ and $R_{13}$ are hydrogen or methyl, X and Z are

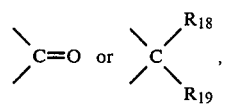

$R_{18}$ being preferably hydrogen or methyl and $R_{19}$ hydrogen or ethoxycarbonyl, Y is

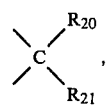

in which $R_{20}$ is preferably hydrogen or $C_1-C_{12}$-alkyl and $R_{21}$ is hydrogen, $C_1-C_{12}$-alkyl, benzyl, 3,5-di-t-butyl-4-hydroxybenzyl, $-OH$, $-NO_2$ or $-NH_2$, and m and n are zero or 1.

3. A compound according to claim 1, of the formula

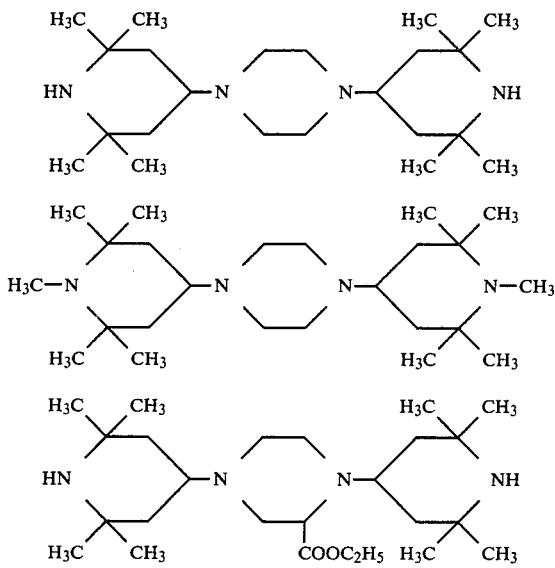

-continued
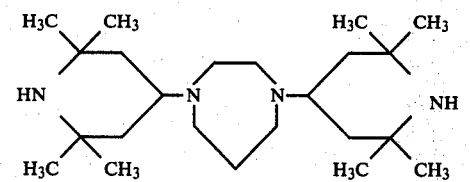
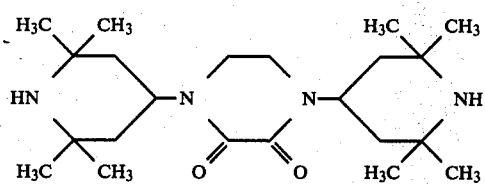
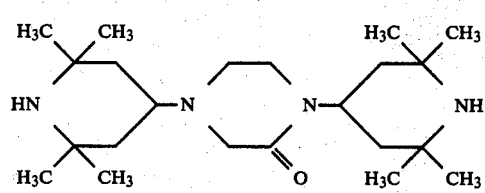
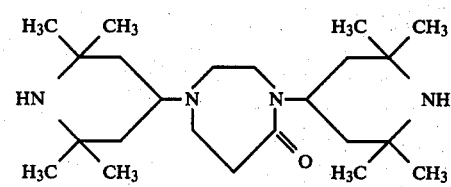
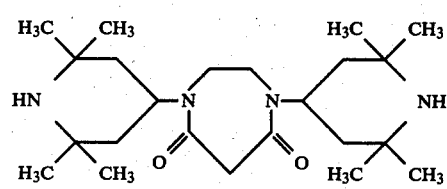
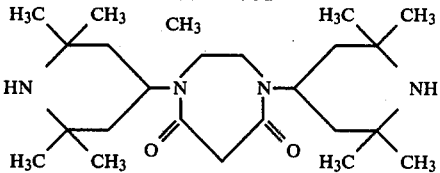
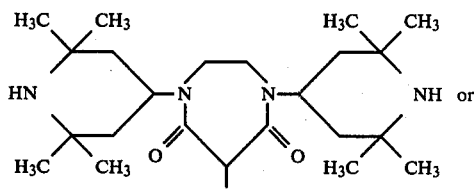
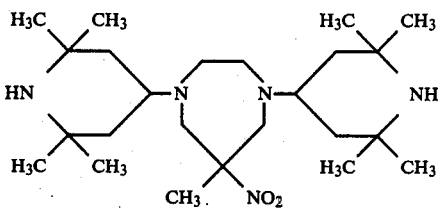
4. A compound according to claim 1, of the formula I, in which $R_2$ and $R_6$ are ethyl, $R_3$, $R_4$ and $R_7$ are methyl and $R_5$ is hydrogen.
5. A compound according to claim 1, of the formula I, in which $R_2$, $R_3$, $R_6$ and $R_7$ are methyl and $R_4$ and $R_5$ are hydrogen.
6. A compound of the formula
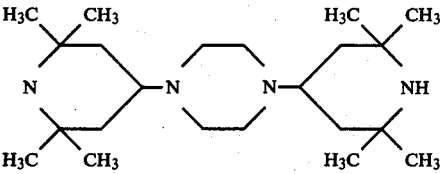
* * * * *